United States Patent [19]

Meguro et al.

[11] Patent Number: 5,143,919

[45] Date of Patent: Sep. 1, 1992

[54] THIENOPYRIDINE DERIVATIVES AND THEIR PHARMACEUTICAL USE

[75] Inventors: Kanji Meguro, Nishinomiya; Hiroyuki Tawada, Takatsuki; Hitoshi Ikeda, Higashiosaka, all of Japan

[73] Assignee: Takeda Chemical Industries, Ltd., Osaka, Japan

[21] Appl. No.: 744,492

[22] Filed: Aug. 13, 1991

[30] Foreign Application Priority Data

Aug. 17, 1990 [JP] Japan .................................. 2-217309
May 23, 1991 [JP] Japan .................................. 3-118444

[51] Int. Cl.[5] .................... A61K 31/435; C07D 495/04
[52] U.S. Cl. .................................... 514/291; 514/301; 546/80; 546/114
[58] Field of Search ................... 546/80, 114; 514/291, 514/301

[56] References Cited

U.S. PATENT DOCUMENTS 3,862,152 1/1975 Kuwada et al. .................... 546/163

FOREIGN PATENT DOCUMENTS 0354994 2/1990 European Pat. Off. .
0386258 9/1990 European Pat. Off. .
1290818 9/1972 United Kingdom .

Primary Examiner—Bernard Dentz
Attorney, Agent, or Firm—Wegner, Cantor, Mueller & Player

[57] ABSTRACT

Thienopyridine derivatives of the formula (I):

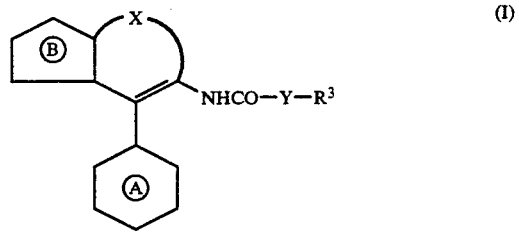

wherein the ring A is an optionally substituted benzene ring; the ring B is an optionally substituted thiophene ring: X is a group of the formula:

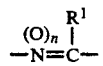

(wherein $R^1$ is hydrogen, alkyl or alkoxy; and n is 0 or 1) or a group of the formula:

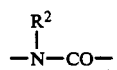

(wherein $R^2$ is hydrogen or alkyl); Y is a single bond, —NH—, alkylene having 1 or 2 carbon atoms or —CH=CH—; and $R^3$ is an optionally substituted hydrocarbon group, or their salts are disclosed. They show strong ACAT inhibitory activities.

23 Claims, No Drawings

//THIENOPYRIDINE DERIVATIVES AND THEIR PHARMACEUTICAL USE

FIELD OF THE INVENTION

The present invention relates to thienopyridine derivatives having excellent acyl-CoA: cholesterol acyltransferase (ACAT) inhibitory activity.

BACKGROUND OF THE INVENTION

Among thienopyridine derivatives, compounds having phenyl group at 4-position with respect to the nitrogen atom of the pyridine, and nitrogen atom bound at 3-position have not been known heretofore in the prior art and it has never been tudied whether they are useful as a medicine for arteriosclerosis or a blood cholesterol lowering agent, or not.

OBJECTS OF THE INVENTION

The main object of the present invention is to provide novel thienopyridine derivatives which have excellent acyl-CoA: cholesterol acyltransferase inhibitory activity to inhibit absorption of cholesterol from the intestinal tract and accumulation of cholesterol at an arterial wall in mammal and are, therefore, useful as a medicine for preventing or treating hypercholesterolemia, atherosclerosis and various diseases caused therefrom (e.g., ischemic heart diseases such as cardiac infarction and the like, and cerebrovascular diseases such as cerebral infarction, cerebral paralysis and the like). Further, the present invention provides an industrially advantageous process for the production of the novel thienopyridine derivatives as well as a pharmaceutical composition containing the novel thienopyridine derivatives.

SUMMARY OR THE INVENTION

The present inventors have intensively studied thienopyridine derivatives. As a result, it has been found that thienopyridine derivatives of the formula (I):

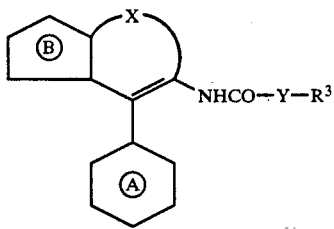
(I)

wherein the ring A is an optionally substituted benzene ring; the ring B is an optionally substituted thiophene ring: X is a group of the formula:

(wherein $R^1$ is hydrogen, alkyl or alkoxy; and n is 0 or 1) or a group of the formula:

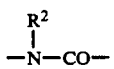

(wherein $R^2$ is hydrogen or alkyl); Y is a single bond, —NH—, alkylene having 1 or 2 carbon atoms or —CH=CH—; and $R^3$ is an optionally substituted hydrocarbon group, or their salts are novel and show strong ACAT inhibitory activities, and they are useful as a blood cholesterol lowering agent and a medicine for treating arteriosclerosis. Thus, the present invention has been completed.

Namely, according to the present invention, there are provided:

(1) a thienopyridine derivative of the formula (I) and a salt thereof;

(2) a compound of the formula (II):

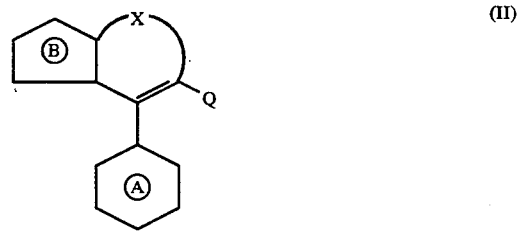
(II)

wherein Q is an optionally esterified or amidated carboxyl group, or —$NH_2$ or —NCO, and the other symbols are as defined above, or a salt thereof;

(3) a process for producing a thienopyridine derivative of the formula (V):

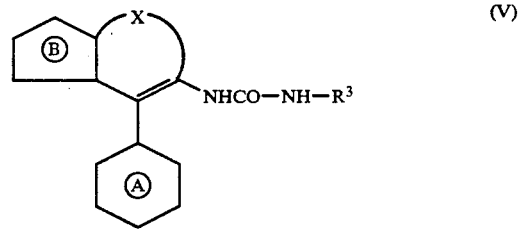
(V)

or a salt thereof which comprises reacting a compound of the formula (III):

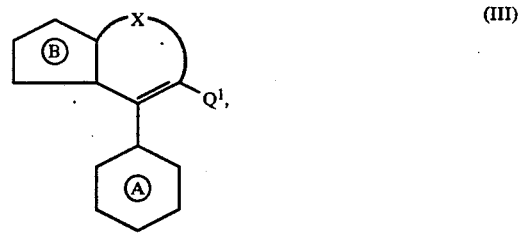
(III)

or a salt thereof with a compound of the formula (IV):

$$R^3—Q^2 \quad (IV),$$

or a salt thereof, wherein either one of $Q^1$ and $Q^2$ is —$NH_2$ and the other is —NCO, and the other symbols are as defined above;

(4) a process for producing a thienopyridine derivative of the formula (VIII):

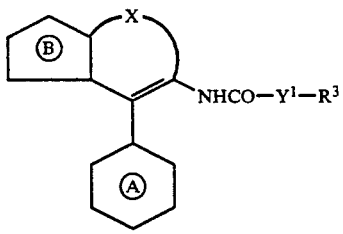

(VIII)

wherein Y¹ is a single bond, an alkylene group having 1 or 2 carbon atoms or —CH=CH—, and the other symbols are as defined above, or a salt thereof which comprises reacting a compound of the formula (VI):

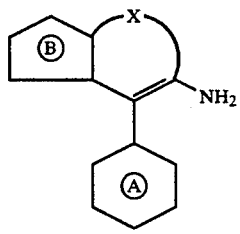

(VI)

wherein all the symbols are as defined above, or a salt thereof with a compound of the formula (VII):

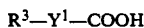  R³—Y¹—COOH    (VII)

wherein all the symbols are as defined above, or a reactive derivative thereof; and (5) an acyl-CoA: cholesterol acyltransferase inhibitor comprising the thienopyridine derivative of the formula (I) or a salt thereof.

DETAILED DESCRIPTION OF THE INVENTION

In the above formulas, the ring A is an optionally substituted benzene ring. Examples of such an substituent include halogen, optionally halogenated alkyl, optionally halogenated alkoxy, optionally halogenated alkylthio, $C_{1-3}$ acyloxy (e.g., formyloxy, acetoxy, propionyloxy group, etc.), hydroxyl, di$C_{1-6}$ alkylamino, mono-$C_{1-6}$ alkylamino and the like. Examples of halogen as the substituent include fluorine, chlorine, bromine and iodine. As the optionally halogenated alkyl group, for example, there can be used straight or branched chain alkyl having 1 to 6 atoms, such an alkyl substituted with 2 to 5 halogen atoms as described above and the like. For example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl, 5-trifluoromethylpentyl and the like are often used. As the optionally halogenated alkoxy and optionally halogenated alkylthio group, for example, there can be used those formed by binding the above alkyl or halogenated alkyl group with oxygen atom and sulfur atom, respectively. For example, optionally halogenated alkoxy such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy, etc., and an optionally halogenated alkylthio such as methylthio, difluoromethylthio, trifluoromethylthio, ethylthio, propylthio, isopropylthio, butylthio, 4,4,4-trifluorobutylthio, pentylthio, hexylthio, etc. are often used. As the di-$C_{1-6}$ alkylamino, there can be used, for example, dimethylamino, methyethylamino, diethylamino, methylpropylamino, ethylpropylamino, dipropylamino and the like. As the mono-$C_{1-6}$ alkylamino, there can be used, for example, methylamino, ethylamino, propylamino and the like.

The ring A may be substituted at any position thereof. When two or more substituents are present, they may be the same or different and the number of the substituents may be 1 to 4. Preferred examples of the substituted ring A include a benzen ring substituted at 2-position with one substituent such as halogen atom (e.g., fluorine, chlorine, etc.), $C_{1-4}$ alkyl (e.g., methyl, ethyl, etc.), $C_{1-4}$ alkoxy (e.g., methoxy, ethoxy, etc.), $C_{1-4}$ alkylthio (e.g., methylthio, etc.) or like.

In the above formulas, the ring B is a thiophene ring which may has a substituent and its sulfur atom may be present at any position except for the positions for condensation with the condensed ring (i.e., the sulfur atom is not the bridgehead atom of the condensed ring). As the substituent, for example, there can be used halogen, alkyl, $C_{3-6}$ cycloalkyl, nitro, amino, acylamino and the like. As the halogen atom, there can be used fluorine, chlorine, bromine and iodine. As the alkyl group, for example, straight or branched alkyl having 1 to 6 carbon atoms are preferred and, for example, there can be used methyl, ethyl, propyl, isopropyl, butyl, isobutyl, sec-butyl, tert-butyl, pentyl, isopentyl, neopentyl, hexyl and the like. As the $C_{3-6}$ cycloalkyl group, for example, there can be used cyclopropyl, cyclopentyl, cyclohexyl and the like.

As the acylamino group, that having 1 to 7 carbon atoms is preferred and, for example, there can be used formylamino, acetylamino, propionylamino, butylylamino, benzoylamino and the like. Such a substituent of the ring B may be the same or different and one or two substituents may be present. Or, the adjacent carbon atoms on the ring B may bind to a group of the formula —(CH$_2$)$_q$— (q is an integer of 3 to 5) to form a 5 to 7 membered ring.

In the above formulas, R³ is a hydrocarbon group which may has a substituent. As the hydrocarbon group represented by R³, for example, there can be used alkyl, cycloalkyl, cycloalkylalkyl, aryl, aralkyl group and the like. As the alkyl group represented by R³, for example, straight or branched alkyl having 1 to 8 carbon atoms are preferred and, for example, there can be used methyl, ethyl, propyl, isopropyl, butyl, isobutyl, sec-butyl, tert-butyl, pentyl, isopentyl, neopentyl, hexyl, heptyl, octyl and the like. As the cycloalkyl group, for example, there can be used $C_{3-6}$ cycloalkyl such as cyclopropyl, cyclopentyl, cyclohexyl and the like. As the cycloalkylalkyl group, for example, there can be used $C_{3-6}$ cycloalkyl-$C_{1-3}$ alkyl such as cyclopropylmethyl, cyclobutylmethyl, cyclopentylmethyl, cyclohexylmethyl and the like. As the aryl group represented by R³, for example, aryl having 6 to 10 carbon atoms such as phenyl, naphthyl or the like is preferred. As the aralkyl group represented by R³, for example, aralkyl having 7 to 16 carbon atoms such as benzyl, 1-phenylethyl, 2-phenylethyl, 1-phenylpropyl, 2-phenylpropyl, 3-phenylpropyl, diphenylmethyl or the like is preferred. Further, these alkyl, cycloalkyl, cycloalkylalkyl, aryl and aralkyl groups represented by R³ may have 1 to 5 substituents which are the same or different. As the substituent, for example, that used in the above ring A is preferably used in addition to the substituents as described hereinafter.

As the aryl group represented by $R^3$, for example, phenyl group or the like is preferred and the phenyl group may have 1 to 5 substituents such as halogen, alkyl, alkoxy, dialkylamino, hydroxyl, acyloxy group and the like. Among them, those having 1 to 5 halogen atoms (e.g. fluorine, chlorine, bromine, iodine), particularly 1 to 5 chlorine or /and fluorine atoms are preferred. For example, 2,4-difluorophenyl or the like is preferred. As the alkoxy group by which the phenyl group may be substituted, for example, $C_{1-4}$ alkyl such as methyl, ethyl, isopropyl or the like is preferably used. Particularly, as the alkyl substituted phenyl, 2,6-dimethylphenyl, 2,6-diethylphenyl, 2-methyl-6-ethylphenyl, 2-methyl-6-isopropylphenyl, 2-ethyl-6-isopropylphenyl, 2,6-diisopropylphenyl preferred. As the alkoxy group by which the phenyl group may be substituted, $C_{1-4}$ alkoxy such as methoxy, ethoxy and or the like is preferably used. As the dialkylamino group by which the phenyl group may be substituted, for example, di-$C_{1-5}$ alkylamino such as dimethylamino, diethylamino, methylethylamino, dipropylamino or the like is preferred. As the acyloxy group by which the phenyl group may be substituted, for example, $C_{1-3}$ acyloxy such as formyloxy, acetony, propionyloxy or the like is preferred. Further, the phenyl group having the above $C_{1-4}$ alkyl or $C_{1-4}$ alkoxy group in combination with hydroxyl or $C_{1-3}$ acyloxy (e.g., formyloxy, acetoxy, etc.), for example, 4-acetoxy-3,5-dimethylphenyl, 4-hydroxy-3,5-dimethylphenyl, 4-acetoxy-3,5-dimethoxyphenyl, 4-hydroxy-3,5-dimethoxyphenyl or the like is preferred as $R^3$.

As the aralkyl group represented by R3, benzyl, 1-phenylethyl and the like are particularly preferred, and its benzene ring is preferably substituted with 1 to 5 substituents such as halogen, alkyl, alkoxy, dialkylamino, hydroxyl, acyloxy group and the like. As the halogen atom, fluorine and chlorine are particularly preferred. Among them, fluorine-substituted aralkyl group, particularly 2,4-difluorobenzyl group is preferred. As the alkyl group, $C_{1-4}$ alkyl such as methyl, ethyl, isopropyl tert-butyl or the like is preferably used. As the alkoxy group, $C_{1-4}$ alkoxy such as methoxy, ethoxy or the like is preferred. As the dialkylamino group, di-$C_{1-5}$ alkylamino such as dimethylamino, diethylamino, methylethylamino, dipropylamino or the like is preferred. As the acyloxy group, $C_{1-3}$ acyloxy such as formyloxy, acetoxy, propionyloxy or the like is preferred. Benzyl having the $C_{1-4}$ alkyl or $C_{1-4}$ alkoxy in combination with hydroxyl or $C_{1-3}$ acyloxy (e.g., formyloxy, acetoxy, etc.), for example, 4-acetoxy-3,5-dimethylbenzyl, 4-hydroxy-3,5-dimethylbenzyl, 4-acetoxy-3,5-dimethoxybenzyl, 4-hydroxy-3,5-dimethoxybenzyl or the like is particularly preferred as $R^3$.

In the above formulas, X is

(wherein $R^1$ is hydrogen, alkyl or alkoxy; and n is 0 or 1) or

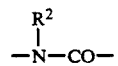

(wherein $R^2$ is hydrogen or an alkyl). Examples of the alkyl group represented by $R^1$ and $R^2$ include a straight or branched chain alkyl having 1 to 6 carbon atoms. For example, there can be used methyl, ethyl, propyl, isopropyl, butyl, isobutyl, sec-butyl, tert-butyl, pentyl, isopentyl, neopentyl, hexyl and the like.

Examples of the alkoxy group represented by $R^1$ include a straight or branched chain alkoxy having 1 to 6 carbon atoms. For example, there can be used methoxy, ethoxy, propoxy, isopropoxy, butoxy, isobutoxy, sec-butoxy, tert-butoxy, pentyloxy, isopentyloxy, neopentyloxy, hexyloxy and the like.

Preferred examples of X include

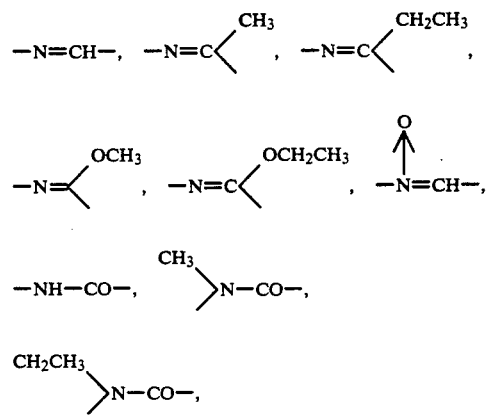

or the like.

In the above formulas, Y is a single bond, —NH—, alkylene having one or two carbon atoms or —CH=CH—. As the alkylene group having one or two carbon atoms, for example, there can be used —CH$_2$—, —CH$_2$CH$_2$—,

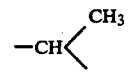

and the like.

Preferred examples of Y include —NH—, —CH$_2$—, —CH$_2$CH$_2$—, —CH=CH—and the like.

The thienopyridine derivative represented by the formula (I) or a salt thereof can be produced, for example, according to the following processes.

Firstly, the compound (III) or a salt thereof is reacted with the compound (IV) or a salt thereof to obtain the compound (V) corresponding to the compound (I) wherein Y is —NH—or a salt thereof. For example, the compound (V) or a salt thereof can be produced (1) by reacting a compound of the formula (IX):

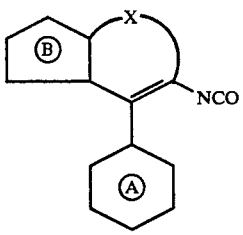 (IX)

wherein the symbols are as defined above, with a compound of the formula (X):

 R₃—NH₂   (X)

wherein the symbol is as defined above, or a salt thereof, or (2) by reacting a compound of the formula (VI)

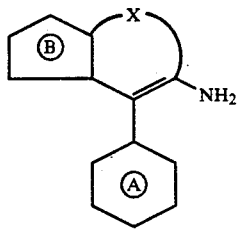 (VI)

wherein the symbols are as defined above, or a salt thereof with a compound of the formula (XI):

 R³—NCO   (XI)

wherein the symbols is as defined above, or a salt thereof.

(3) The compound (VIII) corresponding to the compound (I) wherein Y is a single bond, alkylene having 1 or 2 carbon atoms or —CH═CH—, or a salt thereof can be produced by reacting the compound (VI) or a salt thereof with the compound (VII) or a reactive derivative thereof.

(4) Further, the compound (I) wherein Y is —CH₂CH₂—, or a salt thereof can be produced by reducing the compound (I) wherein Y is —CH═CH—, or a salt thereof. Hereinafter, the above processes (1) to (4) are explained in detail.

Process (1):

In the case of reacting the compound (IX) with the compound (X) or a salt thereof (e.g., a salt with a mineral acid such as hydrochloric acid, sulfuric acid, etc.; a salt with an organic acid such as methanesulfonic acid, benzenesulfonic acid, toluenesulfonic acid, oxalic acid, fumaric acid, malic acid, etc.), the reaction is normally conducted in a solvent. Any solvent can be used as the reaction solvent in so far as it does not interfere with the reaction. For example, ethers (e.g., ethyl ether, isopropyl ether, tetrahydrofuran, dioxane, dimethoxyethane, etc.), aromatic hydrocarbons (e.g., benzene, toluene, xylene, etc.), esters (e.g., methyl acetate, ethyl acetate, etc.), N,N-dimethylformamide, dimethylsulfoxide and the like are preferably used. In the case of using the compound (X) in the form of a salt, the reaction significantly proceeds by desalting, if necessary. As the desalting agent, a tertiary amine such as trimethylamine, triethylamine, N-methylmorpholine or the like, or an aromatic amine such as pyridine, picoline, N,N-dimethylaniline or the like is preferably used. The amount of the amine is 1 to 5 molar equivalent, preferably 1 to 3 molar equivalent per 1 mole of the compound (X). The reaction temperature is normally −10° to 180° C., preferably 0° to 120° C. The reaction time is normally 15 minutes to 40 hours, preferably 30 minutes to 20 hours. The amount of the compound (X) or a salt thereof to be used is 1 to 5 molar equivalent, preferably 1 to 3 molar equivalent per 1 mole of the compound (IX).

Process (2):

The reaction of the compound (VI) or a salt thereof (e.g., a salt with a mineral acid such as hydrochloric acid, sulfuric acid, etc.; a salt with an organic acid such as methanesulfonic acid, benzenesulfonic acid, toluenesulfonic acid, oxalic acid, fumaric acid, malic acid, etc.) with the compound (XI) is conducted under the same conditions as those in the above process (1). In the case of using the compound (VI) in the form of a salt, the same desalting agent as that used in the process (1) can be used. The amount of the compound (XI) to be used is normally 1 to 5 molar equivalent, preferably 1 to 3 molar equivalent per 1 mole of the compound (VI).

Process (3):

In the case of reacting the compound (VI) or a salt thereof (e.g., a salt with a mineral acid such as hydrochloric acid, sulfuric acid, etc.; a salt with an organic acid such as methanesulfonic acid, benzenesulfonic acid, toluenesulfonic acid, oxalic acid, fumaric acid, malic acid, etc.) with the compound (VII), it is normally preferred to use a suitable condensing agent, or to convert the compound (VII) once into a reactive derivative of its carboxyl group and then to react the derivative with the compound (VI) or a salt thereof. As such a condensing agent, for example, there can be used dicyclohexylcarbodimide (DCC), diethyl phosphorocyanidate (DEPC), diphenylphosphoryl azide (DPPA) and the like. When using such a condensing agent, the reaction is preferably conducted in a solvent (e.g., tetrahydrofuran, dioxane, dimethoxyethane, ethyl acetate, benzene, toluene, N,N-dimethylformamide, dimethylsulfoxide, etc.). This reaction can be accelerated in the presence of a base and the reaction is conducted at about −10° to 100° C., pereferably about 0° to 60° C. The reaction time is normally 1 to 96 hours, preferably 1 to 72 hours. The amounts of the compound (VII) and the condensing agent are 1 to 5 molar equivalent, preferably 1 to 3 molar equivalent per 1 mole of the compound (VI) or a salt thereof, respectively. As the base, for example, there can be used alkylamines such as triethylamine and cyclic amines such as N-methylmorpholine, pyridine and the like. The amount of the base to be used is 1 to 5 molar equivalent, preferably 1 to 3 molar equivalent per 1 mole of the compound (VI) or a salt thereof.

As the reactive derivative of the compound (VII), for example, there can be used an acid halide (e.g., chloride, bromide, etc.), an acid anhydride, a mixed acid anhydride (e.g., the anhydride with methylcarbonic acid, the anhydride with ethylcarbonic acid, the anhydride with isobutylcarbonic acid, etc.), an active ester (e.g., the ester with hydroxysuccinimide, the ester with 1-hydroxybenzotriazole, the ester with N-hydroxy-5-norbornene-2,3-dicarboxyimide, the ester with p-nitrophenol, the ester with 8-oxyquinoline, etc.) and the like. Among them, an acid halide is particularly preferred. In the case of reacting the compound (VI) or a salt thereof with the reactive derivative of the compound (VII), the reaction is normally conducted in a solvent (e.g., chloroform, dichloromethane, ethyl ether, tetrahydrofuran, dioxane, dimethoxyethane, ethyl acetate, benzene, toluene, pyridine, N,N-dimethylformamide, etc.). The reaction can be accelerated in presence of a base. The reaction is normally conducted at −10° to 120° C., preferably 0° to 100° C. The reaction time is normally 1 to 48 hours, preferably 1 to 24 hours. The amount of the reactive derivative of the compound (VII) to be used is 1 to 5 molar equivalent, preferably 1 to 3 molar equivalent per 1 mole of the compound (VI) or a salt thereof. As the base, for example, there can be used alkyl amines such as triethylamine and the like, cyclic amines such as N-methylmorpholine, pyridine and the like, aromatic amines such as N,N-dimethylaniline, N,N-diethylaniline and the like, alkali metal carbonates such as sodium carbonate, potassium carbonate and the like, and alkali metal bicarbonates such as sodium bicarbonate, potassium bicarbonate and the like. The amount of the base to be used is 1 to 5 molar equivalent, preferably 1 to 3 molar equivalent per 1 mole of the compound (VI) or a salt thereof.

Further, when a solvent which is immiscible with water is used in this reaction, water can be added to a reaction system to conduct the reaction in a two-phase system.

Process (4):

The compound (I) wherein Y is —CH═CH—, or a salt thereof can be reduced to convert it into the compound (I) wherein Y is —CH₂CH₂—, or a salt thereof.

As a reducing agent to be used, there can be used a metal hydride, for example, lithium alminium hydride, sodium borohydride, lithium borohydride and the like. The amount of the reducing agent is normally 0.5 to 5 molar equivalent, preferably 0.5 to 2 molar equivalent per 1 mole of the compound (I) [Y is —CH═CH—]or a salt thereof. The reaction is normally conducted in a solvent (e.g. methanol, ethanol, ethyl ether, tetrahydrofuran, dioxane, etc.). The reaction temperature is normally −5° to 120° C., preferably 0° to 100° C. The raction time is normally 30 minutes to 12 hours, preferably 30 minutes to 6 hours.

This reduction reaction can also be conducted using a metal and an acid, or a metal and a base or alcohol, instead of using the above reducing agent. In the case of using zinc, tin, iron or the like as the metal, an acid (e.g., hydrochloric acid, sulfuric acid, acetic acid, etc.) can be mainly used as a hydrogen supplying source. Further, in the case of using potassium, sodium, lithium or the like, as the metal, a base (e.g., ammonia, ethylamine, dimethylamine, ethylamine, diethylamine, etc.) as well as an alcohol (e.g., methanol, ethanol, propanol, etc.) can be used as a hydrogen supplying source. The amount of the metal used in this reaction is 1 to 10 molar equivalent, preferably 1 to 5 molar equivalent per 1 mole of the compound (I) [Y is —CH═CH—], or a salt thereof. This reacton is normally conducted in a solvent (e.g., alcohols such as methanol, ethanol, etc.; ethers such as tetrahydrofuran, dioxane, dimethoxyethane, etc.). The above acid or base can also be utilized as the solvent. The reaction temperature is 0° to 120° C., preferably 0° to 80° C. The reaction time is normally 30 minutes to 12 hours, preferably 30 minutes to 6 hours.

This reduction reaction can also be conducted by a catalytic reduction with a catalyst. As the catalyst, for example, there can be used palladium black, palladium carbon, platinum oxide, platinum black, Raney nickel, rhodium carbon and the like. The reaction is normally conducted in a solvent (e.g., methanol, ethanol, isopropanol, tetrahydrofuran, dioxane, dimethoxyethane, formic acid, acetic acid, N,N-dimethylformamide, etc.). The reaction is normally conducted at a pressure of normal pressure to 20 atoms, preferably normal pressure to 5 atoms. The reaction temperature is 0° to 100° C., preferably 0° to 80° C. The reaction time is normally 30 minutes to 24 hours, preferably 30 minutes to 12 hours.

When a lower alkoxy group is contained in the benzene ring of the compound (I) produced according to the above processes (1) to (4), or a salt thereof, if necessary, it can be converted into hydroxyl group, for example, by reacting ht with boron tribromide or the like. This reaction is normally conducted in a solvent (e.g., dichloromethane, chloroform, carbon tetrachloride, benzene, toluene, etc.) at about −20° to 80° C., preferably about 0° to 30° C. The amount of boron tribromide to be used is about 1 to 10 molar equivalent, preferably 1 to 5 molar equivalent per one lower alkoxy group. The reaction time is normally 15 minutes to 24 hours, preferably 30 minutes to 12 hours.

When a hydroxyl group is contained in the benzene ring of the compound (I) produced according to the above processes (1) to (4), or a salt thereof, if necessary, it can be converted into an alkoxy group or an acyloxy group by alkylation or acylation. The alkylation can be conducted by reaction with an alkylating agent such as a halide (e.g., chloride, bromide, iodide, etc.), sulfate or sulfonate (e.g., methane sulfonate, toluenesulfonate, benzenesulfonate, etc.) of an optionally substituted alkane, or the like in a solvent (e.g., methanol, ethanol, propanol, dimethoxyethane, dioxane, tetrahydrofuran, acetone, N,N-dimethylformamide, etc.) in the presence of a base (e.g. an organic base such as trimethylamine, triethylamine, N-methylmorpholine, pyridine, picoline, N,N-dimethylaniline, etc.; an inorganic base such as potassium carbonate, sodium carbonate, potassium hydroxide, sodium hydroxide, etc.). The reaction temperature is normally −10° to 100° C., preferably about 0° to 80° C. The amount of the alkylating agent to be used is about 1 to 5 molar equivalent, preferably about 1 to 3 molar equivalent per 1 mole of the starting phenolic derivative. The reaction time is normally 15 minutes to 24 hours, preferably 30 minutes to 12 hours.

The acylation reaction is conducted by reaction with the desired carboxylic acid or a reactive derivative thereof. This reaction varies depending upon a kind of a particular acylating agent and a kind of a particular starting phenolic derivative, but the reaction is normally conducted in a solvent (e.g., benzene, toluene, ethyl ether, ethyl acetate, chloroform, dichloroethane, dioxane, tetrahydrofuran, N,N-dimethylformamide, pyridine, etc.). In order to accelerate the reaction, an appropriate base (e.g., sodium bicarbonate, potassium bicarbonate, sodium carbonate, potassium carbonate, sodium acetate, triethylamine, pyridine, etc.) can be added. As the reactive derivative of a carboxylic acid, there can be used an acid anhydride, a mixed acid anhydride, an acid halide (e.g., chloride, bromide, etc.) or the like. The amount of the acylating agent to be used is 1 to 5 molar equivalent, preferably 1 to 3 molar equivalent per 1 mole of the starting phenolic derivative. The reaction temperature is normally 0° to 150° C., preferably about 10° to 100° C. The reaction time is normally 15 minutes to 12 hours, preferably 30 minutes to 6 hours.

When the compound (I) is obtained in the free form according to the above processes, for example, it can be converted into a salt with a mineral acid (e.g., hydrochloric acid, sulfuric acid, hydrobromic acid, etc.), an organic acids (e.g. methanesulfonic acid, benzenesulfonic acid, toluenesulfonic acid, oxalic acid, fumaric acid, maleic acid, tartaric acid, etc.) or the like according to a conventional method. When the compound (I) is obtained in the form of a salt, it can be converted into the free form or other salts according to a conventional method.

The desired compound (I) obtained according to the above processes, or a salt thereof can be purified and collected by conventional separation means (e.g. concentration, solvent extraction, column chromatography, recrystallization, etc.).

The compounds (I) or pharmaceutically acceptable salts thereof have an excellent acyl-CoA: cholesterol acyltransferase (ACAT) inhibitory activity, and acute toxicity as well as toxicity due to continuous administration are low. It has been known that ACAT is an enzyme responsible for esterification of cholesterol with a higher fatty acid in cells and plays an important role in absorption of a cholesterol ester at the small intestine. Accordingly, a substance having ACAT inhibitory activity can inhibit adsorption of dietary cholesterol from the intestinal tract, depress increase in blood cholesterol level and intracellular accumulation of cholesterol ester at an arteriosclerotic lesion, as well as prevents evolution of atherosclerosis. Accordingly, the compounds (I) of the present invention having an excellent ACAT inhibitory activity, or salts thereof are useful as safe medicines for preventing and treating hypercholesterolemia, atherosclerosis and various diseases caused thereby (e.g. ischemic cardiopathy such as myocardial infarction, etc.; cerebrovascular disorder such as cerebral infarction, cerebral apoplexy, etc.) in mammal (e.g. mouse, rat, hamster, rabbit, cat, dog, horse, cattle, sheep, monkey, human, etc.).

Among the compounds (I) or salts thereof, those having a lipid peroxidation inhibitory activity (antioxidant activity) are included. It has been known that peroxidation of lipid in the living body has significant relation to crises of arteriosclerosis as well as ischemic diseases in the cerebrovascular and cardiovascular systems. Accordingly, the compounds (I) having both ACAT inhibitory activity and antioxidation activity, or salts thereof are extremely useful as medicines because they can prevent and treat various angiopathy caused by blood cholesterol and peroxylipid.

When the compounds of the formula (I) or pharmaceutically acceptable salts are used as the above medicines, they can be orally or parenterally administered in the form of powders, granules, tablets, capsules, injection preparations and the like obtained by admixing with suitable pharmaceuticallly acceptable carriers, excepients, diluents and the like. When they are used for depressing absorption of cholesterol, oral administration is preferred. The dose varies depending upon a kind of the compounds (I) or salts thereof, administration route, conditions of diseases, age of patients and the like. For example, in the case of oral administration to an adult patient with hypercholesterolemia, a daily dose is about 0.005 to 50 mg/kg body weight, preferably about 0.05 to 10 mg/kg body weight, more preferably about 0.2 to 4 mg/kg body weight and it is preferred that they are administered 1 to 3 times per day with the above daily dose.

The starting compound (VI) or (IX) of the compound (I) of the present invention, or a salt thereof can be advantageously produced, for example, according to the processes as described below or modification thereof.

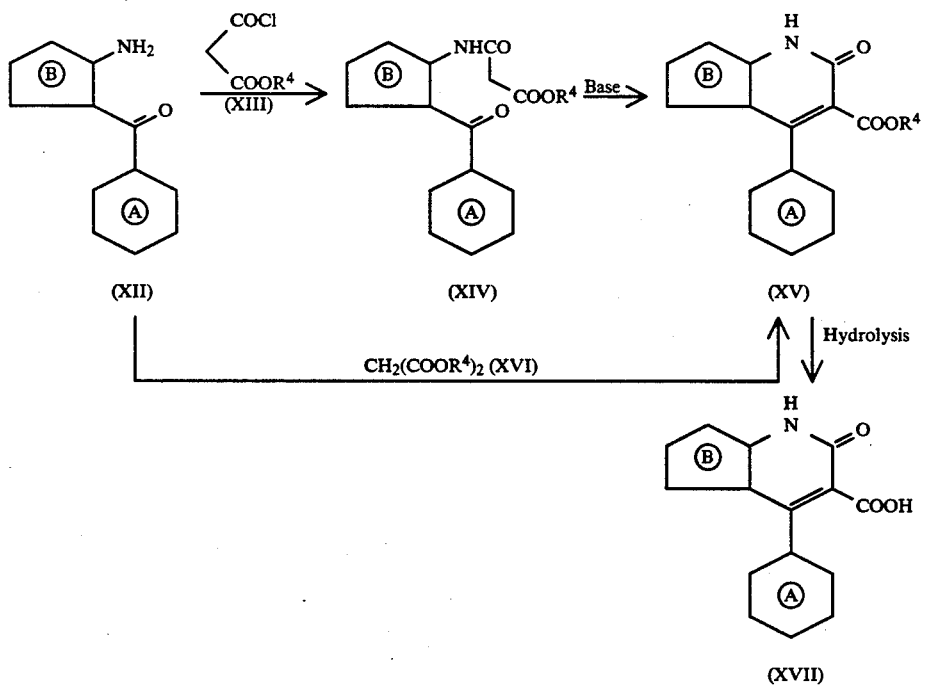

Scheme I (Process A)

-continued
Scheme I (Process A)
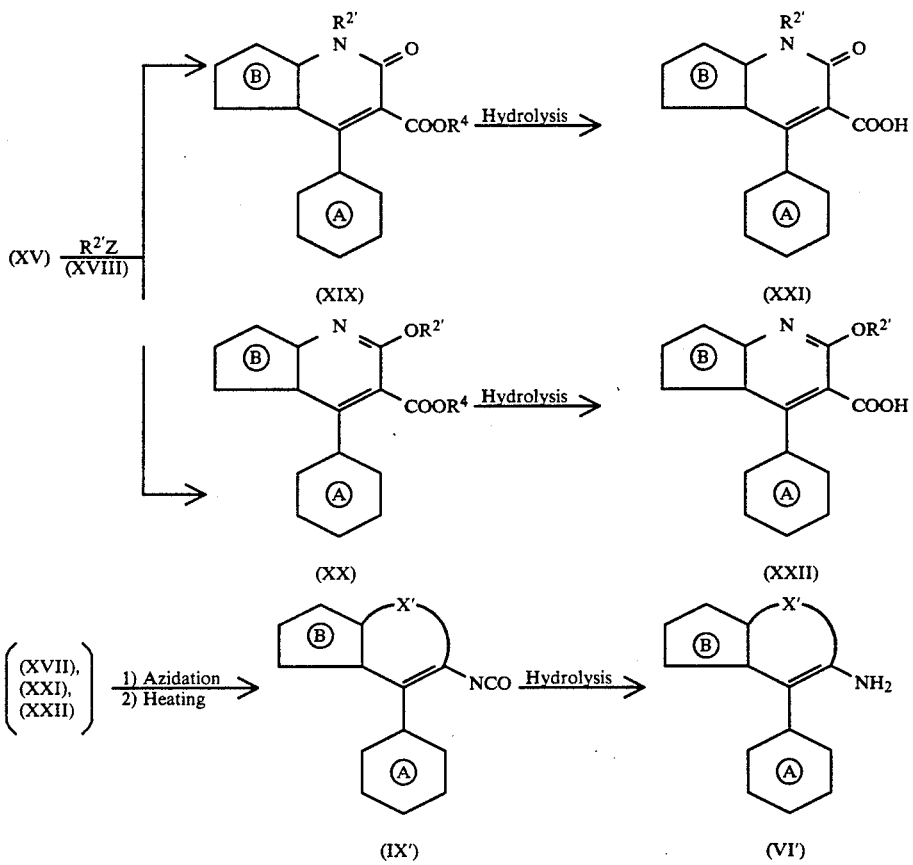
wherein $R^{2'}$ and $R^4$ are an alkyl group, $X'$ is
$$-\underset{H}{\underset{|}{N}}-CO-, \quad -\underset{|}{\underset{R^{2'}}{N}}-CO- \quad \text{or} \quad -N=\underset{|}{\underset{OR^{2'}}{C}}-,$$
Z is a leaving group, and the other symbols are as defined above;
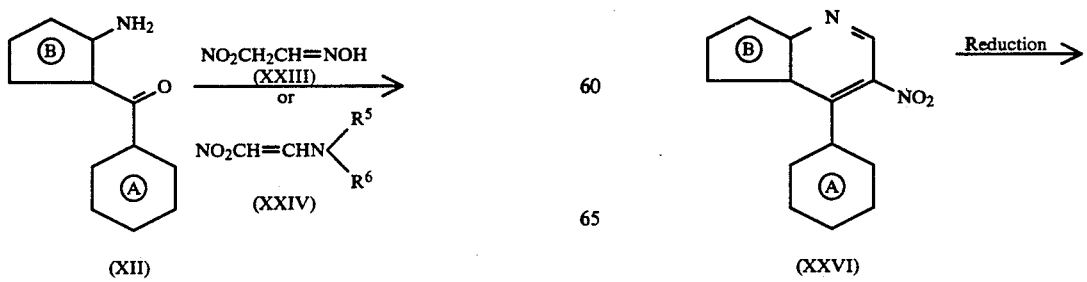
-continued
Scheme II (Process B)
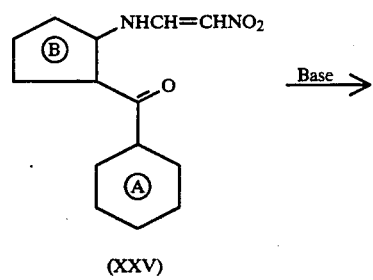

-continued
Scheme II (Process B)

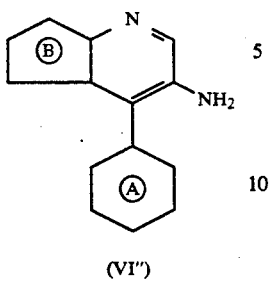

(VI″)

wherein $R^5$ and $R^6$ are the same or different and are an alkyl, phenyl or benzyl, or $R^5$ and $R^6$ may bind each other and form together with the adjacent nitrogen atom a ring, and the other symbols are as defined above.

Scheme III (Process C)

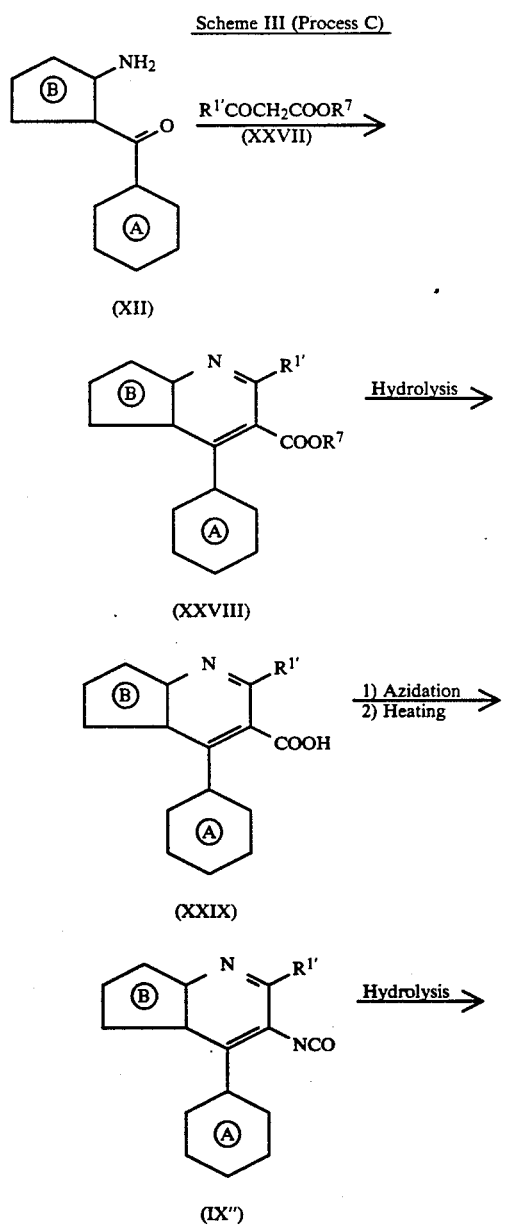

-continued
Scheme III (Process C)

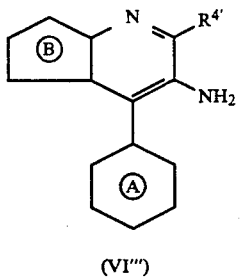

(VI‴)

wherein $R^{1'}$ is hydrogen, or alkyl, $R^7$ is alkyl, and the other symbols are as defined above.

Process A:

As the alkyl group represented by $R^{2'}$ and $R^4$, alkyl having 1 to 4 carbon atoms such as methyl, ethyl, isopropyl butyl or the like is preferred.

In the process A, the compound (XV) can be produced by reacting the aminobenzoylthiophene derivative (XII) with malonic acid diester (XVI), or by reacting the compound (XII) with the compound (XIII) and then dehydrating with a base to cyclize the resultant. In the case of producing the compound (XV) from the compounds (XII) and (XVI), the reaction is normally conducted by heating in the absence of a solvent. This reaction is preferably conducted in the presence of an amine such as piperidine, pyrrolidine, triethylamine, 1,5-diazabicyclo[4.3.0]non-5-ene (DBN), 1,8-diazabicyclo[5.4.0]-7-undecene (DBU),1,4-diazabicyclo[2.2.2]octane (DABCO) or the like, or in the presence of potassium fluoride, cesium fluoride, ammonium tetrabutylfluoride or the like. The reaction temperature is normally about 60° to 220° C., preferably 80° to 200° C. The reaction time is normally 30 minutes to 60 hours, preferably 1 to 24 hours. The amount of the compound (XVI) is about 1 to 5 molar equivalent, preferably about 1 to 3 molar equivalent based on the compound (XII). The reaction of the compound (XII) with the compound (XIII) is normally conducted in a solvent (e.g., ethers such as ethyl ether, tetrahydrofuran, dioxane, dimethoxyethane, etc.; aromatic hydrocarbons such as benzene, toluene, xylene, etc.; esters such as methyl acetate, ethyl acetate, etc.; halogenated hydrocarbons such as dichloromethane, chloroform, etc.; pyridine; dimethylformamide and the like), if necessary, in the presence of a base (e.g., triethylamine, pyridine potassium carbonate, sodium carbonate, potassium bicarbonate, sodium bicarbonate, etc.). In this reaction, a mixed solvent with water can be used, if necessary. The reaction temperature is normally about −20° to 150° C., preferably −10° to 120° C. The reaction time is normally about 10 minutes to 12 hours, preferably 20 minutes to 8 hours. The amount of the compound (XIII) is about 1 to 5 molar equivalent, preferably about 1 to 3 molar equivalent based on the compound (XII). The compound (XIV) formed by this reaction is cyclized by using a base to produce the compound (XV). This reaction is normally conducted in a solvent (e.g., benzene, toluene, xylene, tetrahydrofuran, dioxane, dimethoxyethane, etc.) in the presence of a base (e.g., potassium t-butoxide, sodium methoxide, sodium ethoxide, piperidine, pyrrolidine, triethylamine, DBN, DBU, DABCO, etc.). The reaction temperature is normally about 0° to 200° C., preferably 20° to 170° C. The reaction time is normally about 30 minutes to 12 hours, preferably 1 to 8 hours. The amount of the base to be used is about 0.1 to 3 molar equivalent, preferably 0.1 to 2 molar equivalent based on the compound (XIV). If necessary, for accelerating the reaction, the reaction can also be conducted with removal of water formed in the reaction system by using a Dean-Stark apparatus. The N-alkyl compound (XIX) and/or 0-alkyl compound (XX) are produced by reacting the compound (XV) with the compound (XVIII). This reaction is normally conducted in a solvent (e.g., alcohols such as methanol, ethanol, etc.; ethers such as tetrahydrofuran, dioxane, dimethoxyethane, etc.; ketones such as 2-butanone, etc.; dimethylformamide; dimethylsulfoxide and the like) in the presence of a base (e.g. sodium hydroxide, potassium hydroxide, sodium methoxide, sodium ethoxide, potassium t-butoxide, sodium hydride, sodium amide, potassium carbonate, sodium carbonate, triethylamine, DBU, etc.). Normally, in this process, a mixture of the compounds (XIX) and (XX) is formed and, therefore, these compounds can be used by subjecting the mixture to recrystallization or chromatography to separate them. When suitably selecting a kind of the compound (XVII) and a solvent, or a reaction temperature, sometimes, one of them can be preferentially formed. The reaction temperature is normally about $-5°$ to $150°$ C., preferably about $0°$ to $100°$ C. The reaction time is about 30 minutes to 30 hours, preferably 1 to 15 hours. The amounts of the compound (XVIII) and the base to be used are 1 to 5 molar equivalent, preferably 1 to 2 molar equivalent based on the compound (XV), respectively. Then, the compounds (XV), (XIX) and (XX) are hydrolyzed to obtain the compounds (XVII), (XXI) and (XXII), respectively. This reaction can be normally conducted in a solvent (e.g., alcohols such as methanol, ethanol, propanol, etc.; ethers such as tetrahydrofuran, dioxane, dimethoxyethane, etc.; or a mixed solvent thereof) by using an alkali or alkaline earth metal hydroxide such as sodium hydroxide, potassium hydroxide, barium hydroxide or the like. The reaction temperature is normally about $0°$ to $120°$ C., preferably about $15°$ to $100°$ C. The reaction time is about 30 minutes to 36 hours, preferably about 1 to 20 hours. Then, the carboxylic acids (XVII), (XXI) and (XXII) are converted into acid azides, respectively. Various methods have been known in literatures and any method can be applied to the compounds (XVII), (XXI) and (XXII). For example, by using diphenylphosphorylazide (DPPA) as the acid azides (XVII), (XXI) and (XXII) can be produced by using diphenylphosphorylazide (DPPA) as the azidating agent. This reaction can be normally conducted in an inert solvent (e.g., ethers such as ethyl ether, isopropyl ether, dimethoxyethane, tetrahydrofuran, dioxane, etc.; aromatic hydrocarbons such as benzene, toluene, xylene, etc.; esters such as methyl acetate, ethyl acetate, etc.; ketones such as acetone, 2-butanone, etc.; pyridine; N,N-dimethylformamide and the like). Further, the reaction can be conducted in the presence of a base (e.g., trimethylamine, triethylamine, N-methylmorpholine, etc.) to proceed the reaction. The reaction time is normally about 5 minutes to 12 hours, preferably about 10 minutes to 6 hours. The reaction temperature is normally about $-10°$ to $150°$ C., preferably $-5°$ to $120°$ C. The amount of DPPA to be used is 1 to 3 molar equivalent, preferably 1 to 2 molar equivalent, based on the compound (XVII), (XXI) or (XXII).

The acid azide formed can be isolated and purified by conventional means. However, the reaction mixture is normally heated as it is without isolation of the acid azide to convert it into the isocyanate compound (IX'). For this conversion reaction, it is preferred to use the same solvent as that used for azidation, and the reaction is normally conducted by heating to about $20°$ to $200°$ C., preferably about $30°$ to $150°$ C. The reaction time is normally about 5 minutes to 10 hours, preferably about 5 minutes to 6 hours. The compound (IX') thus obtained can be isolated by conventional means, or used for the production of the compound (I) without isolation thereof, or used as the starting material for the production of the compound (VI'). Namely, the compound (VI') can be obtained by hydrolyzing the compound (IX'). This hydrolysis reaction can be conducted by almost the same conditions as those for the conversion of the above compounds (XV), (XIX) and (XX) into the compounds (XVII), (XXI) and (XXII).

Process B:

As the alkyl group represented by $R^5$ and $R^6$, alkyl having 1 to 4 carbon atoms such as methyl, ethyl, propyl, isopropyl, butyl or the like is preferred. $R^5$ and $R^6$ may bind each other and form together with the nitrogen atom a ring. Examples thereof include 5 to 7 membered rings such as pyrrolidine ring, piperidine ring, homopiperidine ring and the like. Further, such a ring may have additional one oxygen atom and examples thereof include morpholine ring.

The compound (XXV) is produced by the reaction of the compound (XII) with the compound (XXIII) or (XXIV). The reaction is normally conducted in a solvent (e.g., esters such as methyl acetate, ethyl acetate, etc.; ketones such as acetone, 2-butanone, etc.; aromatic hydrocarbons such as benzene, toluene, etc.) in the presence of an acid. As the acid, for example, there can be used hydrochloric acid, hydrobromic acid, sulfuric acid, phosphoric acid, methanesulfonic acid, benzenesulfonic acid, p-toluenesulfonic acid and the like. The acid may be used in its anhydrous form or in the form of a solution. The reaction can be conducted in an uniform system or a two-layer system of a solvent and water. The amount of the compound (XXIII) or (XXIV) to be used is about 1 to 10 molar equivalent, preferably about 1 to 5 molar equivalent based on the compound (XII). Further, the amount of the acid to be used is about 1 to 300 molar equivalent, preferably about 5 to 100 molar equivalent based on the compound (XII). The reaction temperature is normally about $0°$ to $120°$ C., preferably about $10°$ to $100°$ C. The reaction time is about 30 minutes to 15 hours, preferably about 1 to 10 hours. Then, the compound (XXV) is subjected to a cyclization reaction by using a base to produce the compound (XXVI). The cyclization reaction is conducted by the same conditions as those in the production of the compound (XV) from the compound (XIV) in the Process A or modification thereof. Further, the compound (XXVI) is reduced to produce the compound (VI''). As the reducing agent to be used, for example, there can be used lithium aluminum hydride, lithium borohydride and the like. The amount thereof is about 0.5 to 10 molar equivalent, preferably 1 to 5 molar equivalent based on the compound (XXVI). The reaction is normally conducted in a solvent (e.g., methanol, ethanol, ethyl ether, tetrahydrofuran, dioxane, dimethoxyethane, etc.). The reaction temperature is normally about $-5°$ to $120°$ C., preferably about $0°$ to $100°$ C. The reaction time is normally about 15 minutes to 12 hours, preferably 30 minutes to 8 hours.

This reduction reaction can also be conducted by using a metal and an acid, a metal salt and an acid, or an acid and a base, instead of the above reducing agent. As the metal, there can be used zinc, tin, iron and the like and, as the metal salt, there can be used tin(II) chloride and the like. As the hydrogen supplying source, there can be used acids (e.g. hydrochloric acid, sulfuric acid, hydrobromic acid, acetic acid, etc.). In the case of using potassium, sodium, lithium, etc. as the metal, as the hydrogen supplying source, there can be mainly used bases (e.g., ammonia, methylamine, dimethylamine, ethylamine, diethylamine, etc.), as well as alcohols (e.g. methanol, ethanol, propanol, etc.). The amount of the metal or metal salt used in this reaction is about 1 to 20 molar equivalent, preferably about 1 to 10 molar equivalent based on the compound (XXVI). The reaction is normally conducted in a solvent (e.g., alcohols such as methanol, ethanol, etc.; ethers such as tetrahydrofuran, dioxane, dimethoxyethane, etc.). The above acid or base can be utilized as the solvent. The reaction temperature is normally about 0° to 150° C., preferably about 10° to 120° C. The reaction time is normally about 15 minutes to 12 hours, preferably about 30 minutes to 10 hours.

This reduction reaction can also be conducted by a catalytic reduction with a catalyst. As such a catalyst, there can be used palladium black, palladium carbon, platinum oxide, platinum black, Raney nickel, rhodium carbon and the like. The reaction is normally conducted in a solvent (e.g., methanol, ethanol, isopropanol, tetrahydrofuran, dioxane, diethoxyethane, formic acid, acetic acid, N,N-dimethylformamide, etc.). The reaction temperature is about 0° to 120° C., preferably about 10° to 100° C. The reaction pressure is normally at normal pressure to 50 atoms, preferably normal pressure to 10 atoms.

Process C:

As the alkyl group represented by $R^7$, alkyl having 1 to 4 carbon atoms such as methyl, ethyl, propyl, isopropyl, butyl or the like is preferred.

The compound (XXVIII) is produced by the reaction of the compound (XII) with the compound (XXVII). The reaction is normally conducted in a solvent (e.g., alcohols such as methanol, ethanol, propanol, etc.; ethers such as tetrahydrofuran, dioxane, dimethoxyethane, etc.; aromatic hydrocarbons such as benzene, toluene, xylene, etc.; organic acids such as formic acid, acetic acid, propionic acid, etc.). Or, the reaction is conducted without any solvent in the presence of an acid catalyst (e.g., hydrochloric acid, sulfuric acid, hydrobromic acid, methanesulfonic acid, benzenesulfonic acid, p-toluenesulfinic acid, etc.). The amount of the compound (XXVII) to be used is about 1 to 10 molar equivalent, preferably about 1 to 5 molar equivalent based on the compound (XII). Further, the amount of the acid catalyst is about 0.01 to 2 molar equivalent, preferably about 0.05 to 1 molar equivalent. The reaction temperature is normally about 0° to 200° C., preferably about 10° to 150° C. The reaction time is normally about 15 minutes to 24 hours, preferably about 30 minutes to 15 hours. The compound (XXVIII) produced is then converted into the compounds (XXIX), (IX″) and then (VI‴). These reactions can be conducted under the same conditions as those in the Process A or modification thereof.

Further, the starting compound (XII) can also be produced according to the process described in Journal of Medicinal Chemistry, p 214 (1973) or modification thereof.

The compounds (I) of the present invention or salts thereof have an excellent ACAT inhibitory activity. Pharmacological test results are shown hereinafter.

(1) Acyl CoA: Cholesterol Transferase (ACAT) Inhibitory Activity

Experimental Method

An enzyme specimen ACAT was prepared from a microsome fraction of the tunica mucosa intestini tenuis of Spregue-Dawley male rat (six week old) which had been subjected to fasting for 20 hours according to the method described in Journal of Lipid Research, 24, 1127 (1982).

ACAT activity was calculated by measuring an amount of a labeled cholesterol ester formed from [1-$^{14}$C]oleoyl-CoA and endogenous cholesterol according to the process of Helgerud et al. [Journal of Lipid Research, 22, 271 (1981)].

Results

ACTA inhibitory activity of compounds tested are shown in Table 1 by a labeled cholesterol ester formation inhibitory rate (%) obtained by addition of the test compounds in an amount of $10^{-6}$M.

TABLE 1

| Test compound (Example No.) | ACAT inhibitory rate (%) $10^{-6}$M |
| --- | --- |
| 1 | 98.7 |
| 2 | 74.3 |
| 3 | 96.6 |
| 4 | 93.6 |
| 5 | 93.9 |
| 6 | 96.3 |
| 7 | 34.4 |
| 8 | 94.4 |
| 9 | 60.2 |
| 10 | 95.1 |
| 11 | 94.5 |
| 12 | 82.3 ($0.5 \times 10^{-6}$M) |
| 13 | 97.5 |
| 14 | 91.9 |

As is seen from Table 1, the compounds (I) or salts thereof have an excellent ACAT inhibition.

The following Reference Examples and Examples further illustrate the present invention in detail but are not to be construed to limit the scope thereof.

In the following Examples and Reference Examples, elution of column chromatography was conducted with monitoring by TLC (thin layer chromatography). For monitoring by TLC, Kieselgel 60F$_{254}$ manufactured by Merck Co. was employed as a TLC plate. The developing solvent was the same as that used for elution of column chromatography and a UV detector was employed for the detection. Kieselgel 60 (70 to 230 mesh) manufactured by Merck Co. was used for a silica gel column.

The abbreviations used in Examples and Reference Examples are as follows:

mg : milligram, g : gram, ml : milliliter, mp : melting point.

All the percents are by weight unless otherwise stated and room temperature is about 15° to 25° C.

EXAMPLE 1

To a solution of 5-amino-4-(2-chlorophenyl)-2-ethylthieno[2,3-b]pyridine (288 mg) in tetrahydrofura ml) was added 2,4-difluorophenyl isocyanate (0.13 ml) and the mixture was stirred at room temperature for 18 hours, and then the solvent was distilled off. To the residue was added isopropyl ether to obtain N-[4-(2-chlorophenyl)-2-ethylthieno[2,3-b]pyridin-5-yl]-N'-(2,4-d as crystals (416 mg, 93.9 %). Colorless prisms were obtained by recrystallization from acetone-hexane, mp: 217°-218° C.

Elemental analysis for $C_{22}H_{16}ClF_2N_3OS$, Calcd.: C, 59.53; H, 3.63; N, 9.47; Found: C, 59.57; H, 3.60; N, 9.44

EXAMPLE 2

To a mixture o 4-acetoxy-3,5-dimethoxycinnamic acid (638 mg), dimethylformamide (2 drops) and tetrahydrofuran (8 ml) was added oxazolyl chloride (0.25 ml). The mixture was stirred at room temperature for one hour and then the solvent was distilled off to obtain 4-acetoxy-3,5-dimethoxycinnamic acid chloride as crystals. To a solution of the crystals in dichloromethane (15 ml) were added 5-amino-4-(2-chlorophenyl)-2-ethylthieno[2,3-b]pyridine (576 mg) and N,N-dimethylaniline (0.25 ml) with ice cooling. After warming to room temperature, the mixture was stirred for 5 hours, washed in turn with water, aqueous saturated $NaHCO_3$ solution and water, and then dried over $MgSO_4$. The solvent was distilled off and the residue was crystallized from ethanol (729 mg, 67.4%). 5-(4-Acetoxy-3,5-dimethoxycinnamoylamino)-4-(2-chloropheny ethylthieno[2,3-b]pyridine was obtained as colorless prisms by recrystallization from acetone, mp: 133°-135° C.

Elemental analysis for $C_{28}H_{25}ClN_2O_5S \cdot 2/3(CH_3)_2CO$, Calcd.: C,62.12; H, 5.14; N, 4.83; Found: C, 62.24; H, 5.19; N, 4.71

EXAMPLE 3

To a mixture of 4-(2-chlorophenyl)-6,7-dihydor-2-ethyl- 7-methyl-6-oxothieno[2,3-b]pyridine-5-carboxylic acid (347 mg), diphenylphosphoryl azide (330 mg) and benzene (4 ml) was added dropwise triethylamine (0.14 ml). The mixture was stirred at room temperature for 30 minutes, stirred under reflux for 30 minutes and then 2,4-difluoroaniline (0.12 ml) was added. The mixture was refluxed for 4 hours, washed with water, dried over $MgSO_4$, and then the solvent was distilled off. The residue was chromatographed on a silica gel and eluted with chloroform/ethyl acetate/metanol (9 : 1 : 0.25). The solvent was distilled off to obtain N-[4-(2-chlorophenyl)-6,7-dihydro-2-ethyl-7-meth oxothieno[2,3-b]pyridin-5-yl]-N'-(2,4-difluorophenyl)urea as colorless powder (210 mg, 44.4%).

Elemental analysis for $C_{23}H_{18}ClF_2N_3O_2S$, Calcd.: C, 58.29; H, 3.83; N, 8.87; Found : C, 58.60; H, 4.06; N, 8.59

EXAMPLE 4

According to the same manner as that described in Example 1, N-(4-chlorophenyl)-N'-[4-(2-chlorophenyl)-2-ethylthieno[2,3-b]pyridin-5-yl]urea colorless needles (99.3%), mp: 230°-231° C.

Elemental analysis for $C_{22}H_{17}Cl_2N_3OS$, Calcd.: C, 59.73; H, 3.87; N, 9.50; Found : C, 59.70; H, 3.86; N, 9.47

EXAMPLE 5

According to the same manner as that described in Example 1, N-[4-(2-chlorophenyl)-2,3-dimethylthieno[2,3-b]pyridin-5-yl]-N'-(2,4-difluropheny colorless prisms (91.0%), mp: 202°-203° C.

Elemental analysis for $C_{22}H_{16}ClF_2N_3OS$, Calcd.: C, 59.53; H, 3.63; N, 9.47; Found : C, 59.72; H, 3.62; N, 9.54

EXAMPLE 6

According to the same manner as that described in Example 1, N-[4-(2-chlorophenyl)-6,7-dihydro-5H-cyclopenta-[1',2':5,4]thieno[2,3-b]pyridin-3-yl]-N'-(2,4-difluorophenyl)urea was obtained as colorless prisms (88.8%), mp: 223°-224° C.

Elemental analysis for $C_{23}H_{16}ClF_2N_3OS$, Calcd.: C, 60.59; H, 3.54; N, 9.22; Found : C, 60.38; H, 3.47; N, 9.19

EXAMPLE 7

To a solution of 3-amino-4-(2-chlorophenyl)-6,7-dihydro-5H-cyclopenta[1',2':5,4]thieno[2,3-b]pyridine (150 mg) and N,N-dimethylaniline (0.065 ml) in dichloromethane (3 ml) was added dropwise 2,4-difluorobenzoyl chloride (0.07 ml) with ice-cooling. The mixture was stirred for 10 minutes with ice-cooling and then stirred at room temperature for 2 hours. Then, the mixture was washed in turn with water, aqueous saturated $NaHCO_3$ solution and water, and dried over $MgSO_4$ The solvent was distilled off to obtain 4-(2-chlorophenyl)-3-(2,4-difluorobenzoylamino)-6,7 -dihydro-5H-cyclopenta[1',2':5,4]thieno[2,3-b]pyridine (206 mg, 93.6%) as crystals. The crystals were recrystallized from acetone to obtain colorless prisms, mp: 219°-220° C.

Elemental analysis for $C_{23}H_{15}ClF_2N_2OS$, Calcd.: C, 62.66; H, 3.43; N, 6.35; Found : C, 62.60; H, 3.58; N, 6.31

EXAMPLE 8

According to the same manner as that described in Example 2, 4-(2-chlorophenyl)-3-(2,4-difluorophenylacetylamino)-6,7-dihydro-5H-cyclopenta-[1', 2,3-b]pyridine (89.4%) was obtained, mp:127°-128° C.

Elemental analysis for $C_{24}H_{17}ClF_2N_2OS$, Calcd.: C, 63.36; H, 3.77; N, 6.16; Found : C, 63.49; H, 4.00; N, 6.27

EXAMPLE 9

According to the same manner as that described in Example 1, N-(2,4-difluorophenyl)-N'-[4-(2-methylphenyl)-thieno[2,3-b]pyridin-5-yl]urea was obtained as colorless needles (91.7%), mp: 223°-224° C. (recrystallized from ethanol).

Elemental analysis for $C_{21}H_{15}F_2N_3OS$, Calcd.: C, 63.79; H, 3.82; N, 10.63; Found : C, 63.75; H, 4.03; N, 10.60

EXAMPLE 10

According to the same manner as that described in Example 1, N-[4-(2-chlorophenyl)-2-methylthieno[2,3-b]pyridin-5-yl]-N'-(2,4-difluorophenyl)urea was obtained as colorless needles (88.1%), mp: 196°-198° C.

Elemental analysis for $C_{21}H_{14}ClF_2N_3OS$, Calcd.: C, 58.68; H, 3.28; N, 9.77; Found : C, 58.90; H, 3.25; N, 9.74

EXAMPLE 11

To a mixture of 5-amino-2-chloro-4-(2-methylphenyl)thieno[2,3-b]pyridine hydrochloride ethanol solvate (160 mg) and tetrahydrofuran (3 ml) were added dropwise triethylamine (0.07 ml) and 2,4-difluorophenyl isocyanate (0.12 ml). The mixture was stirred at room temperature for 5 hours and the solvent was distilled off. Water was added to the residue and the mixture was extracted with ethyl acetate. The extract was washed with water and dried over $MgSO_4$ and the solvent was distilled off. To the residue was added isopropyl ether to obtain N-[2-chloro-4-(2-methylphenyl)-thieno[2,3-b]pyridin-5-yl]-N'-[2,4-difluorophenyl)urea (133 mg, 68.9%) as crystals. crystals were recrystallized from ethanol to obtain colorless prisms, mp; 225°–226° C.

Elemental analysis for $C_{21}H_{14}ClF_2N_3OS$, Calcd.: C, 58.68; H, 3.28; N, 9.77; Found : C, 58.78; H, 3.41; N, 9.59

EXAMPLE 12

According to the same manner as that described in Example 1, N-[4-(2-chlorophenyl)-5,6,7,8-tetrahydro[1]-benzothieno[2,3-b]pyridin-3-yl]-N'-(2,4-difluorophenyl)urea was obtained as colorless prisms (94.9%), mp: 228°–230° C.

Elemental analysis for $C_{24}H_{18}ClF_2N_3OS$, Calcd.: C, 61.34; H, 3.86; N, 8.94; Found : C, 61.62; H, 3.83; N, 8.90

EXAMPLE 13

To a mixture of 4-acetoxy-3,5-dimethylbenzoic acid (270 mg), diphenylphosphoryl azide (DPPA, 430 mg) and benzene (6 ml) was added dropwise triethylamine (0.18 ml) and the mixture was stirred at room temperature for 30 minutes and then at reflux for 40 minutes to obtain a solution of 4-acetoxy-3,5-dimethylphenylisocyanate. To the solution was added 5-amino-2-ethyl-4-(2-methoxyphenyl)-thieno[2,3-b]pyridine (284 mg) and the mixture was heated under reflux for 5 hours. The mixture was washed with water and dried over MgSO$_4$ and the solvent was distilled off. To the residue was added ethanol to obtain N-(4-acetoxy-3,5-dimethylphenyl)-N'-[2-ethyl-4-(2-methoxyphenyl)-thien[2,3-b]pyridin-5-yl]urea (350 mg, 71.6%) as crystals. The crystals were recrystallized from ethanol to obtain colorless needles, mp: 217°–218° C.

Elemental analysis for $C_{27}H_{27}N_3O_4S$, Calcd.: C, 66.24; H, 5.56; N, 8.58; Found : C, 66.55; H, 5.57; N, 8.18

EXAMPLE 14

According to the same manner as that described in Example 13, N-(4-acetoxy-3,5-dimethoxyphenyl)-N'-[2-ethyl-4-(2-methoxyphenyl)thieno[2,3-b]pyridin-5-yl]urea was obtained as colorless needles (60.8%), mp: 244°–245° C.

Elemental analysis for $C_{27}H_{27}N_3O_6S$, Calcd.: C, 62.17; H, 5.22; N, 8.06; Found : C, 62.22; H, 5.31; N, 7.99

EXAMPLE 15

According to the same manner as that described in Example 13, N-(4-dimethylaminophenyl)-N'-[2-ethyl-4-(2-methoxypenyl)thieno[2,3-b]pyridin-5-yl]urea was obtained as colorless needles (74.4%), mp: 208°–209° C. (recrystallized from acetone).

Elemental analysis for $C_{25}H_{26}N_4O_2S$, Calcd.: C, 67.24; H, 5.87; N, 12.55; Found : C, 67.18; H, 5.85; N, 12.44

REFERENCE EXAMPLE 1

(1) A mixture of 2-amino-3-(2-chlorobenzoyl)-5-ethylthiophene (5.30 g), 1-morpholino-2-nitroethene (3.16 g), 6N HCl (5 ml) and acetone (25 ml) was stirred at room temperature for one hour. Water was added to the mixture, which was extracted with ethene acetate. The extract was washed with water and dried over MgSO$_4$, and then the solvent was distilled off to obtain 3-(2-chlorobenzoyl)-2-(2-nitroethenylamino)-5-ethylthiophene as crystals (5.65 g, 84.1%). The crystals were recrystallized from acetone to obtain yellow plates, mp: 125°–126° C.

Elemental analysis for $C_{15}H_{13}ClN_2O_3S$, Calcd.: C, 53.49; H, 3.89; N, 8.32; Found : C, 53.52; H, 3.91; N, 8.32

(2) To a solution of DBU (5.1 g) in benzene (50 ml) was added dropwise a solution of 3-(2-chlorobenzoyl)-2-(2-nitroethenylamino)-5-ethylthiophene (5.1 g) in dioxane-benzene (1 : 1, 30 ml) over one hour with stirring under reflux. After refluxing for additional one hour, the mixture was washed with water and dried over MgSO$_4$. The solvent was distilled off and to the residue was added isopropyl ether to obtain 4-(2-chlorophenyl)-2-ethyl-5-nitrothieno[2,3-b]pyridine as crystals (4.3 g, 89.0%). The crystals were recrystallized from isopropyl ether to obtain pale yellow prisms, mp: 72°–73° C.

Elemental analysis for $C_{15}H_{11}ClN_2O_2S$ Calcd.: C, 56.52; H, 3.48; N, 8.79; Found : C, 56.53; H, 3.48; N, 8.79

(3) To a mixture of 4-(2-chlorophenyl)-2-ethyl-5-nitrothieno[2,3-b]pyridine (4.0 g), dioxane (25 ml) and conc. hydrochloric acid (12.5 ml) was added tin(II) chloride dihydrate (8.5 g). After stirring at room temperature for one hour, water was added to the mixture, which was made strong alkaline with 6N NaOH and then extraced with chloroform. The extract was washed with water and dried over MgSO$_4$ and the solvent was distilled off. The residue was chromatographed on a silica gel column and eluted with hexane-ethyl acetate (4 : 1). The solvent was distilled off and to the residue was added hexane to obtain 5-amino-4-(2-chlorophenyl)-2-ethylthieno[2,3-b]pyridine (3.1 g, 85.6%) as crystals. The crystals were recrystallized from isopropyl ether to obtain colorless prisms, mp: 87°–88° C.

Elemental analysis for $C_{15}H_{13}ClN_2S$, Calcd.: C, 62.38; H, 4.54; N, 9.70; Found : C, 62.49; H, 4.57; N, 9.70

REFERENCE EXAMPLE 2

(1) A mixture of 2-amino-3-(2-chlorobenzoyl)-5-ethylthiophene (5.30 g), ethylmalonyl chloride (4.50 g) and benzene (60 ml) was heated under reflux for one hour, washed with water and dried over MgSO$_4$, and then the solvent was distilled off. To the residue was added hexane to obtain 3-(2-chlorobenzoyl)-2-ethoxycarbonylacetylamino-5-ethylthiophene as crystals (7.1 g, 93.7%}. The crystals were recrystallized from isopropyl ether to obtain colorless prisms, mp: 56°–57° C.

Elemental analysis for $C_{18}H_{18}ClNO_4S$, Calcd.: C, 56.91; H, 4.79; N, 3.69; Found : C, 56.78; H, 4.73; N, 3.86

(2) To a solution of DBU (5.2 g) in toluene (50 ml) was added dropwise a solution of 3-(2-chlorobenzoyl)-2-ethoxycarbonylacetylamino-5-ethylthiophene (6.5 g) in toluene (30 ml) over one hour with stirring under reflux. After refluxing for 7 hours, the mixture was washed with water and dried over MgSO$_4$, and then the solvent was distilled off. The residue was chromatographed on a silica gel column and eluted with hexane-acetone (5 : 1). The solvent was distilled off and hexane was added to obtain ethyl 4-(2-chlorophenyl)-6,7-dihydro-2-ethyl-6-oxothieno[2,3-b]pyridine-5-carboxylate as crystals 33.1%). The crystals were recrystallized from ethanol to obtain light yellow prisms, mp: 126°–127° C.

Elemental analysis for $C_{18}H_{16}ClN_3OS$, Calcd.: C, 59.75; H, 4.46; N, 3.87; Found : C, 59.78; H, 4.52; N, 3.85

(3) To a mixture of 4-(2-chlorophenyl)-6,7-dihydro-2-ethyl-6-oxothieno[2,3-b]pyridine-5-carboxylate (1.80 g), potassium carbonate (0.7 g) and DMF (15 ml) was added dropwise methyl iodide (0.37 ml). After stirring at room temperature for 1.5 hours, water was added to the mixture, which was extracted with ethyl acetate. The extract was washed with water and dried over MgSO$_4$, and then the solvent was distilled off. To the residue was added isopropanol to obtain ethyl 4-(2- chlorophenyl)-6,7-dihydro-2-ethyl-7-methyl-6-oxo-thieno[2,3-b]pyridine-5-carboxylate as crystals (1.32 g, 70.6%). The crystals were recrystallized from isopropyl ether to obtain colorless needles, mp: 105°–106° C.

Elemental analysis for $C_{19}H_{18}ClNO_3S$, Calcd.: C, 60.71; H, 4.83; N, 3.73; Found: C, 60.53; H, 4.91; N, 3.62

(4) A mixture of ethyl 4-(2-chlorophenyl)-6,7-dihydro-2-ethyl-7-methyl-6-oxothieno[2,3-b]pyridine-5-carboxylate (1.10 g), KOH (0.49 g) and 80% ethanol (10 ml) was heated at 80° C. for 20 minutes and water was added. Then, the mixture was made acidic with 2N HCl and extracted with ethyl acetate. The extract was washed with water and dried over $MgSO_4$, and then the solvent was distilled off. To the residue was added hexane to obtain 4-(2-chlorophenyl)-6,7-dihydro-2-ethyl-7-methyl-6-oxothieno[2,3-b]pyridine-5-carboxylic acid as crystals (0.91 g, 89.3%). The crystals were recrystallized from ethanol to obtain colorless prisms, mp: 155°–156° C.

Elemental analysis for $C_{17}H_{14}ClNO_3S$, Calcd.: C, 58.70; H, 4.06; N, 4.03; Found : C, 58.72; H, 4.06; N, 4.01

According to the same manner as that described in Reference Example 1, the following compounds of Reference Examples 3 to 9.

REFERENCE EXAMPLE 3

(1) 3-(2-Chlorobenzoyl)-4,5-dimethyl-2-(2-nitroethenylamino)thiophene, mp: 171°–173° C.

(2) 4-(2-Chlorophenyl)-2,3-dimethyl-5-nitro-thieno[2,3-b]pyridine, mp: 136°–137° C.

(3) 5-Amino-4-(2-chlorophenyl) 3-dimethyl-thieno [2,3-b]pyridien, mp: 117°–118° c.

REFERENCE EXAMPLE 4

(1) 3-(2-Chlorobenzoyl)-5,6-dihydro-2-(2-nitroethenylamino)-4H-cyclopenta[b]thiophene, mp: 118°–120° C.

(2) 4-(2-Chlorophenyl)-6,7-dihydro-3-nitro-5H-cyclopenta[1',2':5,4]thieno[2,3-b]pyridine, mp: 118°–119° C.

(3) 3-Amino-4-(2-chlorophenyl)-6,7 dihydro-5H-cyclopenta[1',2':5,4]thieno[2,3-b]pyridine, mp: 130°–131° C.

REFERENCE EXAMPLE 5

(1) 3-(2-Methylbenzoyl)-2-(2-nitroethenylamino)-thiophene, mp: 155°–156° C.

(2) 4-(2-Methylphenyl)-5-nitrothieno[2,3-b]pyridine, mp: 111°–112° C.

(3) 5-Amino-4-(2-methylphenyl)thieno[2,3-b]pyridine, mp: 98°–99° C.

REFERENCE EXAMPLE 6

(1) 3-(2-Chlorobenzoyl)-5-methyl-2-(2-nitroethenylamino)thiophene, mp: 160°–162° C.

(2) 4-(2-Chlorophenyl)-2-methyl-5-nitrothieno[2,3-b]pyridine, mp: 157°–158° C.

(3) 5-Amino-4-(2-chlorophenyl)-2-methylthieno[2,3-mp: 114°–115° C.

REFERENCE EXAMPLE 7

(1) 5-Chloro-3-(2-methylbenzoyl)-2-(2-nitroethenylamino)thiophene, mp: 160°–162° C.

(2) 2-Chloro-4-(2-methylphenyl)5-nitrothieno[2,3-b]pyridine, mp: 126°–127° C.

(3) 5-Amino-2-chloro-4-(2-methylphenyl)thieno[2,3-b]pyridine hydrochloride ethanol solvate, mp: 114°–115° C.

REFERENCE EXAMPLE 8

(1) 3-(2-Chlorobenzoyl)-2-(2-nitroethenylamino)- o 4,5,6,7-tetrahydrobenzo[b]thiophene, mp: 163°–164° C.

(2) 4-(2-Chlorophenyl)-3-nitro-5,6,7,8-tetrahydro[1-]benzothieno[2,3-b]pyridine, mp: 157°–159° C.

(3) 3-Amino-4-(2-chlorophenyl)-5,6,7,8-tetrahydro[1-]benzothieno[2,3-b]pyridine, mp: 148°–150° C.

REFERENCE EXAMPLE 9

(1) 5-Ethyl-3-(2-methoxybenzoyl)-2-(2-nitro ethenylamino)thiophene, mp: 140°–141° C.

(2) 2-Ethyel-4-(2-methoxyphenyl)-5-nitro-thieno[2,3-b]pyridine, mp: 116°–117° C.

(3) 5-Amino-2-ethyl-4-(2-methoxyphenyl)thieno[2,3-b]pyridine, mp: 91°–92° C.

What is claimed is:

1. A thienopyridine derivative of the formula (I):

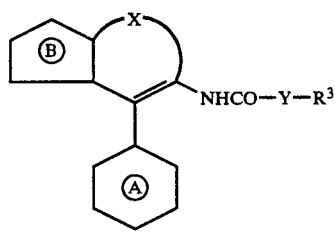
(I)

wherein the ring A is an optionally substituted benzene ring; the ring B is an optionally substituted thiophene ring: X is a group of the formula:

(wherein $R^1$ is hydrogen, alkyl or alkoxy; and n is 0 or 1) or a group of the formula:

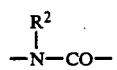

(wherein $R^2$ is hydrogen or alkyl); Y is a single bond, —NH—, alkylene having 1 or 2 carbon atoms or —CH=CH—; and $R^3$ is an optionally substituted hydrocarbon group, or its salt.

2. A thienopyridine derivative according to claim 1, wherein the ring A is benzene or benzene having 1 to 4 substituents selected from the group consisting of halogen, $C_{1-4}$ alkyl, $C_{1-4}$ alkoxy and $C_{1-4}$ alkylthio.

3. A thienopyridine derivative according to claim 1, wherein the ring B is thiophene or thiophene having 1 or 2 substituents selected from the group consisting of halogen, $C_{1-6}$ alkyl, $C_{3-6}$ cycloalkyl, nitro, amino and $C_{1-7}$ acylamino, or the adjacent carbon atoms on the ring B may bind to a group —$(CH_2)_q$—(wherein q is an integer of 3 to 5) to form a 5 to 7 membered ring.

4. A thienopyridine derivative according to claim 1, wherein $R^3$ is $C_{1-8}$ alkyl, $C_{3-6}$ cycloalkyl, $C_{3-6}$ cycloalkyl-$C_{1-3}$ alkyl, $C_{6-10}$ aryl or $C_{7-16}$ aralkyl, which may have 1 to 5 substituents selected from the group consisting of halogen, $C_{1-4}$ alkyl, $C_{1-4}$ alkoxy, $C_{1-4}$ alkylthio, hydroxyl, $C_{1-3}$ acyloxy and di-$C_{1-5}$ alkylamino.

5. A thienopyridine derivative according to claim 1, wherein X is

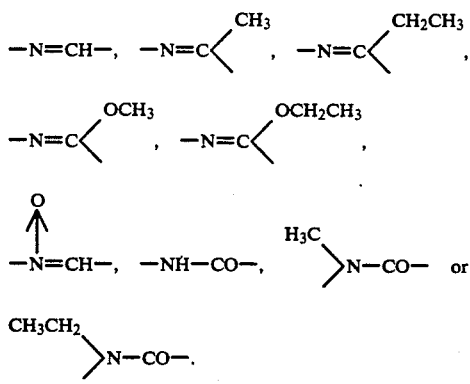

6. A thienopyridine derivative according to claim 1, wherein Y is a single bond, —NH—, —CH₂—, —CH₂CH₂— or —CH=CH—.

7. A thienopyridine derivative according to claim 1 which is N-[4-(2-chlorophenyl)-2-ethylthieno[2,3-b]pyridin-5-yl]-N'-(2,4-difluorophenyl)urea.

8. A thienopyridine derivative according to claim 1 which is 5-(4-acetoxy-3,5-dimethoxycinnamoylamino)-4-(2-chlorophenyl)-2-ethylthieno[2,3-b]pyridine.

9. A thienopyridine derivative according to claim 1 which is N-[4-(2-chlorophenyl)-6,7-dihydro-2-ethyl-7-methyl-6-oxothieno[2,3-b]pyridin-5-yl]-N'-(2,4-difluoro-phenyl) urea.

10. A thienopyridine derivative according to claim 1 which is N-(4-chlorophenyl)-N'-[4-(2-chlorophenyl)-2-ethylthieno[2,3-b]pyridin-5-yl]urea.

11. A thienopyridine derivative according to claim 1 which is N-[4-(2-chlorophenyl)-2,3-dimethylthieno[2,3-b]pyridin-5-yl]-N'-(2,4-difluorophenyl)urea.

12. A thienopyridine derivative according to claim 1 which is N-[4-(2-chlorophenyl)-6,7-dihydro-5H-cyclopenta[1',2':5,4]thieno[2,3-b]pyridin-3-yl]-N'-(2,4-difluorophenyl)urea.

13. A thienopyridine derivative according to claim 1 which is 4-(2-chlorophenyl)-3-(2,4-difluorobenzoylamino)-6,7-dihydro-5H-cyclopenta[1'2':5,4]thieno[2,3-b]pyridine.

14. A thienopyridine derivative according to claim 1 which is 4-(2-chlorophenyl)-3-(2,4-difluorophenylacetylamino]-6,7-dihydro-5H-cyclopenta[1',2':5,4]thieno[2,3-b]pyridine.

15. A thienopyridine derivative according to claim 1 which is N-(2,4-difluorophenyl)-N'-[4-(2-methylphenyl)-thieno[2,3-b]pyridin-5-yl]urea.

16. A thienopyridine derivative according to claim which is N-[4-(2-chlorophenyl)-2-methylthieno[2,3-b]pyridin-5-yl]-N'-(2,4-difluorophenyl)urea.

17. A thienopyridine derivative according to claim which is N-[2-chloro-4-(2-methylphenyl)thieno[2,3-b]pyridin-5-yl]-N'-(2,4-difluorophenyl)urea.

18. A thienopyridine derivative according to claim 1 which is N-[4-(2-chlorophenyl)-5,6,7,8-tetrahydro[1-]benzothieno[2,3-b]pyridin-3-yl]-N'-(2,4-difluorophenyl)urea.

19. A thienopyridine derivative according to claim 1 which is N-(4-acetoxy-3,5-dimethylphenyl)-N'-[2-ethyl-4-(2-methoxyphenyl)thieno[2,3-b]pyridin-5-yl]urea.

20. A thienopyridine derivative according to claim 1 which is N-(4-acetoxy-3,5-dimethoxyphenyl)-N'-[2-ethyl-4-(2-methoxypheyl)thieno[2,3-b]pyridin-5-yl]urea.

21. A thienopyridine derivative according to claim 1 which is N-(4-dimethylaminophenyl)-N'-[2-ethyl-4-(2-methoxyphenyl)thieno[2,3-b]pyridin-5-yl]urea.

22. An acyl-CoA: cholesterol acyltransferase inhibitor comprising a thienopyridine derivative of the formula (I) as claimed in claim 1, or a pharmaceutically acceptable salt thereof combined with a pharmaceutically acceptable carrier, diluent or excipient.

23. A method for inhibiting acyl-CoA: cholesterol acyltransferase comprising administrating an effective amount of a thienopyridien derivative of the formula (I) as claimed in claim 1, or a pharmaceutically acceptable salt thereof optionally together with a pharmaceutically acceptable carrier, diluent or excipient to a patient requiring such inhibition.

* * * * *

UNITED STATES PATENT AND TRADEMARK OFFICE
CERTIFICATE OF CORRECTION

PATENT NO. : 5,143,919

DATED : September 1, 1992

INVENTOR(S) : Kanji MEGURO et al.

It is certified that error appears in the above-identified patent and that said Letters Patent is hereby corrected as shown below:

Column 28, line 10 (claim 16, line 1), change "claim" to --claim 1--.

Column 28, line 13 (claim 17, line 1), change "claim" to --claim 1--.

Signed and Sealed this

Twenty-sixth Day of April, 1994

Attest:

BRUCE LEHMAN

*Attesting Officer*   *Commissioner of Patents and Trademarks*